(12) United States Patent
Nakao (10) Patent No.: US 7,175,648 B2
(45) Date of Patent: Feb. 13, 2007

(54) DEEP ENDOSCOPIC STAPLE AND STAPLER

(75) Inventor: Naomi L. Nakao, New York, NY (US)

(73) Assignee: Granit Medical Innovations, LLC, New York, NY (US)

( * ) Notice: Subject to any disclaimer, the term of this patent is extended or adjusted under 35 U.S.C. 154(b) by 454 days.

(21) Appl. No.: 10/716,107

(22) Filed: Nov. 18, 2003

(65) Prior Publication Data

US 2005/0107807 A1 May 19, 2005

(51) Int. Cl.
*A61B 17/08* (2006.01)
*A61D 1/00* (2006.01)

(52) U.S. Cl. ............ 606/220; 606/142; 606/151; 606/219

(58) Field of Classification Search ........ 606/142, 606/143, 151, 216, 219, 217, 220, 221; 411/446
See application file for complete search history.

(56) References Cited

U.S. PATENT DOCUMENTS

| | | | |
|---|---|---|---|
| 3,120,230 A | * | 2/1964 | Shold ................ 606/158 |
| 4,064,881 A | * | 12/1977 | Meredith ............ 606/142 |
| 4,509,937 A | * | 4/1985 | Ledvina et al. ...... 606/158 |
| 4,667,823 A | * | 5/1987 | Wolfe et al. ......... 206/392 |
| 5,015,249 A | * | 5/1991 | Nakao et al. ........ 606/142 |
| 5,049,153 A | * | 9/1991 | Nakao et al. ........ 606/151 |
| 5,222,961 A | * | 6/1993 | Nakao et al. ........ 606/143 |
| 5,306,283 A | * | 4/1994 | Conners ............. 606/151 |
| 5,392,978 A | * | 2/1995 | Velez et al. ........ 227/177.1 |

\* cited by examiner

*Primary Examiner*—Michael J. Hayes
*Assistant Examiner*—Michael G. Mendoza
(74) *Attorney, Agent, or Firm*—R. Neil Sudol; Henry D. Coleman; William J. Sapone (57) ABSTRACT

An endoscopic staple and related stapling device that can be used in conjunction with flexible or rigid endoscopy. The staple can also be used for other surgical procedures. The invention relates to performing a stapling operation on internal body tissues as part of a surgical procedure, diagnostic procedure or therapeutic procedure. This invention includes a surgical staple, an associated staple holder, and an associated staple delivery and deployment device. The staple holder and delivery system have a design iteration whereby the holder can be reloaded with additional staples to be used on the same patient. There is another design iteration whereby the staple holder and stapler are reusable after appropriate cleaning and sterilization.

23 Claims, 12 Drawing Sheets

DEEP ENDOSCOPIC STAPLE AND STAPLER

FIELD OF THE INVENTION

The present invention relates to endoscopy and, more particularly, to a staple and a device used to secure or staple tissue inside the human body with said staple and device working in conjunction with a flexible endoscope.

BACKGROUND OF THE INVENTION

Surgeons have developed a number of methods and techniques to treat a variety of medical anomalies in the abdomen and gastrointestinal tract. These procedures often involve stapling and must be performed during open surgery or rigid laparoscopic surgery because there is no device or reliable method for placing staples using flexible endoscopes. Suturing has the same current limitations and as such the medical community is unable to perform surgical procedures via natural body openings using flexible endoscopes. Surgical procedures for removing diseased organs, gastric bypass surgery performed in morbidly obese patients, and a variety of other surgical procedures must be performed during open or laparoscopic surgery.

Providing the physicians with a flexible stapling device to be used in conjunction with a flexible endoscope would significantly reduce the length and complexity of the surgery. Consequently, morbidity and mortality would be reduced; hospital stay shortened, and cost savings provided. Because flexible endoscopic procedures are typically performed under conscious sedation and are much less invasive, they are naturally less traumatic to the body. Convalescence is significantly shortened, postoperative pain is virtually eliminated and patients are ambulatory within hours after an endoscopic procedure.

The only means of treating a problem that requires surgery in the abdomen is through open or laparoscopic surgery. Bypass and gastric restrictive surgery for the morbidly obese patient is being performed during open or laparoscopic surgery. These operations take five to seven hours and are performed under general anesthesia. The recovery typically takes six weeks to three months if the operation is successful. Recently, a new procedure has been introduced during which a band is placed around the stomach. This operation is less complex than the abovementioned procedures but is also being performed through open or laparoscopic means.

These complex and invasive surgical procedures require general anesthesia, surgical incisions, multiple days in the hospital, and significant use of medication for postoperative pain and lengthy periods of convalescence. Surgical procedures to treat morbidly obese patients have a high incidence of complications and thus limit the number of patients that can benefit from these procedures. These operations are currently performed through a large abdominal incision. The physician excludes or closes off a large portion of the stomach. In addition, a portion of the small intestine is bypassed, and a new connection to the stomach is made. Oftentimes the patient has had prior surgery causing adhesions, which bind the intestines together. The surgeon has to dissect these adhesions and free the bowel in order to get to the operative site. This procedure is quite difficult, and has to be performed before the actual bypass and gastric stapling operation has even begun. This surgery can also be performed laparoscopically. However, while the incisions are smaller, the abdomen is filled with a large amount of gas in order to distend it and enable the surgeon to perform the operation. The surgery is more difficult and typically takes two to three hours longer than the open operation. This requires longer anesthesia time increasing the danger to the patient. The distended abdomen impinges on the patient's lungs decreasing breathing capacity and adding morbidity. While this is a less invasive procedure than open surgery, it still entails significant complications and lengthy patient convalescence. Furthermore, because the surgery takes longer than open surgery, risk to the patient is increased from prolonged general anesthesia. The less traumatic banding procedure is less complicated, however reports of band slippage and postoperative infection exist. In addition, results have been poor.

OBJECTS OF THE INVENTION

It is an object of this invention to provide a medical instrument for closing openings internal to a patients body utilizing flexible or rigid endoscopes inserted into the body primarily, though not exclusively, through existing body orifices.

It is another object of the invention to provide a surgical procedure for closing openings internal to a patient's body, which is quicker, safer and less invasive than the conventional surgical procedures, thereby, significantly reducing patient morbidity and mortality.

It is a further object of this invention to provide a means to entirely eliminate external scars from surgery because the entire operation is to be performed inside the body and through an existing orifice.

It is another object of this invention to reduce anesthesia time, strength of anesthetics used, post operative pain, hospital stay and convalescence time, particularly with respect to operations closing openings internal to a patients body.

It is a further object of this invention to provide a staple used to close or clamp tissue within the body that can be passed through a flexible endoscope.

It is another object of this invention to provide a staple delivery instrument that can be used in conjunction with flexible and rigid endoscopes with a working channel diameter no larger than 3.8 millimeters.

It is yet another object of this invention to provide a long, flexible staple delivery device that can be passed deep into the organ to be operated upon.

It is also an object of this invention to provide a special staple that will enter into the organ deeply enough to hold the desired tissues together, and with a closure strong enough to keep these tissues securely affixed to one another.

These and other objects of the invention will be apparent from the drawings and descriptions herein. Every object of the invention is believed to be attained by at least one embodiment of the invention. However, there is not necessarily any single embodiment that achieves all of the objects of the invention.

SUMMARY OF THE INVENTION

In accordance with the present invention, there is provided an endoscopic staple and related stapling device that can be used in conjunction with flexible or rigid endoscopy. The staple can also be used during other surgical procedures. The invention relates to performing a stapling operation on internal body tissue as part of a surgical procedure, diagnostic procedure or therapeutic procedure. This invention includes a surgical staple, an associated staple holder, and an associated staple delivery and deployment device. The staple holder and delivery system have a design iteration whereby the holder can be reloaded with additional staples to be used on the same patient. There is another design iteration whereby the staple holder and stapler are reusable after appropriate cleaning and sterilization.

An endoscopic stapling assembly for securing tissue internal to the body, utilizing a flexible endoscope, comprises, in accordance with the present invention, a staple for clamping or securing tissue inside of the body and a locking element operatively engageable with the staple for securing the staple in a closed position once staple is positioned and closed on desired tissue. The stapling assembly additionally comprises a tubular member providing a working channel for active stapler components, and a stapler holder connected to the tubular member for holding the staple during deployment thereof and manipulating the staple into an open or closed position. The active stapler components are operatively connected to the staple holder for operating the same. The assembly further comprises means such as a tray for holding additional staples to facilitate loading of the additional staples into the staple holder.

The staple, preferably made of a shape memory or flexible material is insertable into tissue for clamping together opposing segments of tissue. Preferably, the staple is biased to an open position having an open-position angle greater than an open-position angle of the staple holder.

Pursuant to a further feature of the present invention, the staple is provided with notches along a backside of the staple to guide, accept, and secure a locking element in the form of a backbone or brace. The backbone is made of rigid material having a pair of legs or prongs slidable over a backside of the staple and securable firmly over the closed staple. The backbone legs have inwardly extending protrusions engageable in the notches or recesses provided in the staple for locking into place over the closed staple. The jaws of the staple holder are re-loadable with additional staples and backbone locking elements from the staple-holding tray.

The staple is preferably configured with opposing legs of a single folded-over material, the legs being formed in an arc configuration and having pointed distal tips that touch one another when the staple is in a closed position.

To secure the staple in a closed position, an actuator in the form of a push bar is provided for advancing the backbone over the staple, the push bar being connected to a handle mechanism at a proximal end of the tube providing the working channel.

The staple holder may specifically comprise formed metal components connected to a drive-wire and handle mechanism. The formed metal components may be comprised of opposing jaws, whereby opposing edges or inner surfaces of the jaws are formed to securely hold the staple, and wherein the jaws are adapted to enter and grasp tissue.

Pursuant to an additional feature of the present invention, the distal ends of the jaws are pointed for enabling the jaws to enter targeted tissue. The staple holder includes means for operating the jaws to clamp the staple closed over the tissue, the jaws being provided along mutually facing surfaces with grooves for seating the staple and allowing for the backbone to slide over the closed staple.

The staple-holding tray is provided with preformed holes to securely hold staples in an open configuration and is also provided with orientation structure for maintaining a plurality of backbones at proximal ends of the staples in the tray. The backbones are engageable with the respective staples to maintain the staples in a closed post-firing configuration.

A staple assembly for use in rigid or flexible endoscopy for securing tissue internal to the body comprises, in accordance with the present invention, means for clamping or securing tissue inside of the body, and means, engageable with the means for clamping or securing, for locking the staple in a closed position once the staple is positioned and closed on desired tissue.

In a preferred embodiment of the invention, the means for clamping or securing tissue inside of the body comprises a staple capable of being opened and closed. The staple is biased to an open position and has an open position angle that is is greater then an open position angle of a staple holder component. The staple may include opposing legs of a single folded-over member, the legs being formed in an arc configuration and having pointed distal tips that touch when the legs are in a closed position. In addition, the means for locking includes a backbone element, the staple having notches along a back of the staple to guide, accept, and secure the backbone to the staple.

An endoscopic staple and stapler assembly for securing tissue internal to the body comprises, in accordance with a specific embodiment of the present invention, a staple holder component and a staple capable of being opened and closed. The staple is releasably held by the staple holder component and is biased to an open position. The staple has a biased open position angle that is greater then an open position angle of the staple holder component. The staple is made from shape memory or flexible metal and has opposing legs of a single folded-over member, the legs being formed in an arc configuration. The staple legs have pointed distal tips that touch when the staple is in a closed position, the distal tips of the legs being pointed for the purpose of clamping or entering tissue for securing tissue inside of the body. The endoscopic staple and stapler assembly further includes a backbone made of rigid material that is slidable over a backside of the staple. The staple has notches or recesses along a backside to guide, accept, and secure the backbone firmly over the staple in a closed position once the staple is positioned and closed on desired tissue. A push bar is included in the endoscopic staple and stapler assembly for advancing the backbone over the staple, the push bar being temporarily effectively coupled to the backbone. The staple holder component includes a pair of opposing jaws formed to securely hold the staple, adapted to enter and grasp tissue, and attached to a drive mechanism that opens and closes the jaws. The jaws hold the staple securely, grasp targeted tissue, and clamp the staple closed over the tissue while the backbone is slid over the closed staple. An elongate tube has a distal end connected to the jaw mechanism and a proximal end connected to an actuation and handle mechanism. The tube has at least one lumen and is made of a flexible material, for providing a working channel for active stapler components, securely connected to the staple holder. A handle mechanism provided for actuation and manipulation is securely connected to the elongate tube and operatively connected to the push bar.

The present invention is directed in part to a tray provided with a plurality of first preformed holes adapted to securely hold staples in an open configuration. The tray also includes a plurality of second preformed holes aligned with respective ones of the first preformed holes for maintaining staple-locking backbones disposed in a prelocking position on proximal ends of respective ones of the staples, the tray serving to facilitate loading of the staples and backbones into a staple-holding jaw mechanism of a stapling device.

BRIEF DESCRIPTION OF THE DRAWINGS

A complete understanding of the present invention may be obtained by reference to the accompanying drawings, when considered in conjunction with the subsequent, detailed description, in which.

For purposes of clarity and brevity, like elements and components will bear the same designations and numbering throughout the FIGURES.

DEFINITIONS

The term "endoscopic" is used herein to designate any of a variety of minimally invasive surgical procedures wherein optical elements are used to view internal spaces and tissues of the patient through relatively small, natural or surgically created openings in a patient. Concomitantly, the term "endoscope" as used herein refers to any optical instrument inserted through such a small opening for purposes of enabling visualization of internal tissues during a minimally invasive procedure.

An endoscopic stapling device as described herein is inserted through a working channel of an endoscopic instrument. An "endoscopic instrument" may include optical illumination and image transmission components or may be a simple tube, such as a cannula. More generally, an endoscopic instrument may be any instrument that is used to perform an endoscopic diagnostic or surgical procedure.

The term "open position angle" refers herein to the most open configuration of a staple or a pair of jaws. Two relatively inclined elements (legs, prongs, jaws) subtending a larger open position angle than another two relatively inclined elements means that the first two elements naturally open to a wider extent than the second two elements.

The term "backbone" as used herein denotes a locking element that is engageable with a staple or clip to hold the staple or clip in a closed configuration in the tissues of a patient. The term "backbone" is more particularly meant to designate a locking element that fits along the back or outside of a spring-biased staple to provide rigidity and stability to the staple in a closed configuration. Preferably, a staple used with a backbone as described herein is spring biased by internal stresses of its memory or shape alloy material to an open configuration. The backbone counteracts that spring bias to hold the staple closed upon deployment in organic tissues. In a specific embodiment disclosed herein, a staple backbone comprises a pair of legs pr prongs projecting in parallel to one another, the legs or prongs being provided with inwardly extending protrusions for mating with similarly shaped notches or recesses in respective staple legs to secure the backbone to the staple. The staple in addition or alternatively may be provided along outer surfaces of its own legs or prongs with grooves that receive the legs or prongs of the backbone in a seating relationship.

The term "active stapler components" refers herein generally to movable components of an endoscopic stapling device, which move during use of the device to effect various steps in an endoscopic stapling procedure. Those steps include, but are not necessarily limited to, ejection of a staple holder, the opening and closing of staple holder jaws, the insertion of a staple holder and an entrained staple into internal organic tissues of a patient, the movement of a backbone over a staple, the removal of staple jaws from a deployed and locked staple.

DESCRIPTION OF THE PREFERRED EMBODIMENTS

Figure 1:
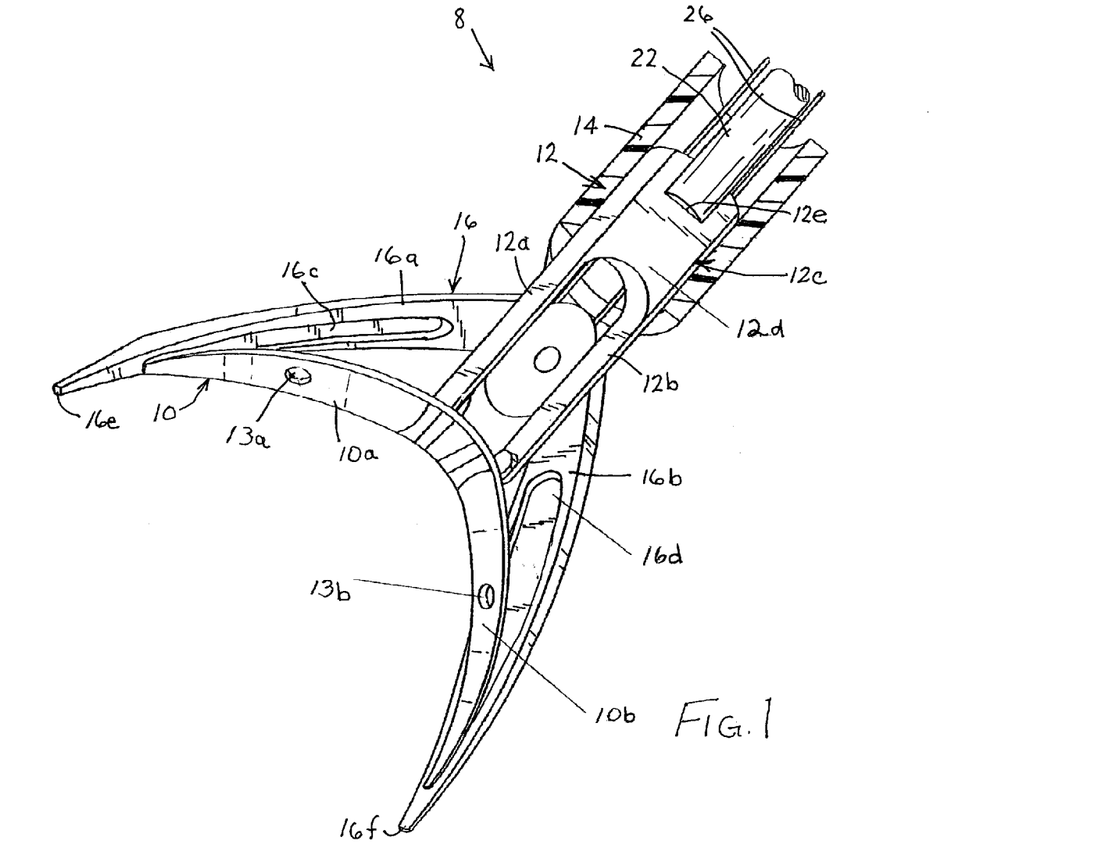
FIG. 1 is a schematic perspective view, of a cross-section of an endoscopic stapling device in accordance with the present invention, showing a staple, a backbone, and a staple holder mechanism, in an open position.

FIG. 1 is a perspective view, partly in cross section, of a distal end of an endoscopic stapling device or assembly 8 for use in inserting a staple 10 deeply into internal organic tissues of a patient. Staple 10 includes a pair of legs or prongs 10a and 10b each provided with a staple notch, aperture, or recess 13 for enabling a locking of the staple in a closed post-firing configuration. Staple 10 is locked in the closed configuration by a backbone 12 (see FIGS. 2–5) comprising a pair of legs or prongs 12a and 12b projecting parallel to one another from a body portion 12c. Body portion 12c has opposing planar faces 12d and is provided at a rear or proximal end with a cutout or recess 12e serving as a seat or receptacle for the distal end of a push bar or elongate flexible pusher member 22. As discussed below, backbone 12 is disposed back behind the staple 10 until the staple is inserted into the tissues and is ready to be locked.

In addition to staple 10, backbone 12 and pushbar 22, endoscopic stapling assembly 8 includes a staple holder 16, an elongate tube 14, and one or more drive wires or rods 26. Staple 10 initially sits within the jaws 16a and 16b of the staple holder 16 with the backbone 12 positioned at a proximal end of the staple 10 and contained within the staple holder 16 and elongate tube 14.

Jaws 16a and 16b of staple holder 16 are formed along inner surfaces (not labeled) with respective longitudinally extending grooves or recesses 16c and 16d for removably receiving legs 10a and 10b of staple 10. Grooves 16c and 16d may be approximately the same size and shape as staple legs 10a and 10b, for seating the staple so as to prevent a forward or lateral displacement of the staple from the staple holder 16 prior to completion of a staple closing operation.

Staple 10 is biased to an open position angle greater than the open position angle of staple holder 16, thus exerting outward pressure on staple holder 16 and serving to maintain staple 10 within staple holder 16 in an open configuration of the staple and the staple holder. This force contributes to staple retention and maintaining staple 10 in position inside the staple holder 16 when staple 10 and staple holder 16 are inserted into the targeted tissue to be secured. Backbone 12 contributes to staple 10 maintaining the preferred position inside staple holder 16 jaws by providing resistance against staple 10 and keeping staple 10 from sliding proximally as these components are inserted into tissue. Staple holder 16 is connected to elongate tube 14 and an actuation assembly, which includes drive wires or rods 26 that activate the jaws 16a and 16b of the staple holder 16. Elongate tube 14 contains push bar 22 which slides distally to push backbone 12 over staple 10 after the staple and the holder 16 have been inserted into tissues, as discussed below with reference to FIGS. 6–9. Push bar 22 is operatively connected to a component of a handle mechanism 24 (FIGS. 10A–10E) which controls the forward motion of the push bar 22.

Figure 2:
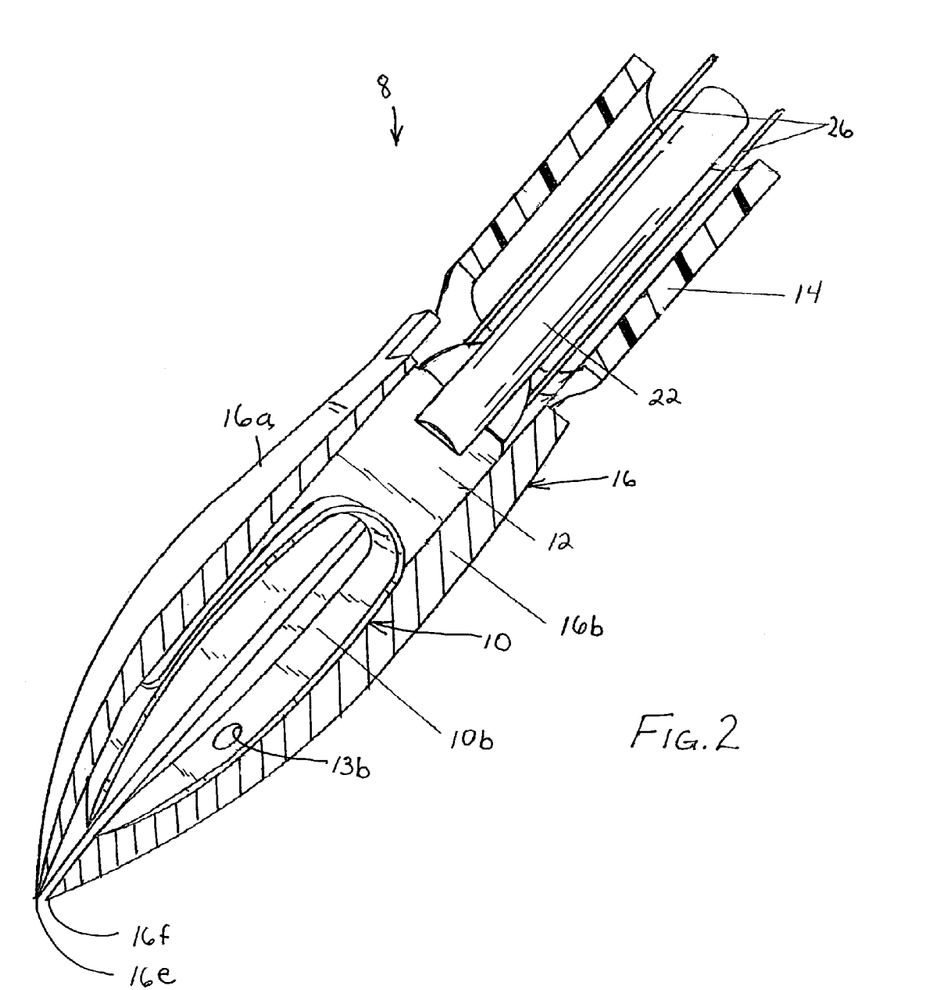
FIG. 2 is a schematic perspective view, similar to FIG. 1, showing the endoscopic stapling device of that drawing figure in a closed position.

FIG. 2 is a cross sectional view of the distal end of endoscopic stapling assembly 8, showing staple 10 with staple notches 13a and 13b in legs 10a and 10b, backbone 12 with two protrusions 15a and 15b extending inwardly from respective legs or prongs 12a and 12b, staple holder 16, elongate tube 14, drive wires 26, and push bar 22, with staple 10 and holder 16 disposed in a closed position. After the insertion of holder 16 and staple 10 into target tissues inside a patient, backbone 12 is slid forward over the closed staple 10 and locked into position by means of staple notches 13a and 13b and backbone protrusions 15a and 15b. Staple holder 16 is made from a rigid metal with opposing jaws that meet and align when closed. The closing of staple holder 16 jaws results in the closing of staple 10 and alignment of staple legs 10a and 10b.

Figure 3:
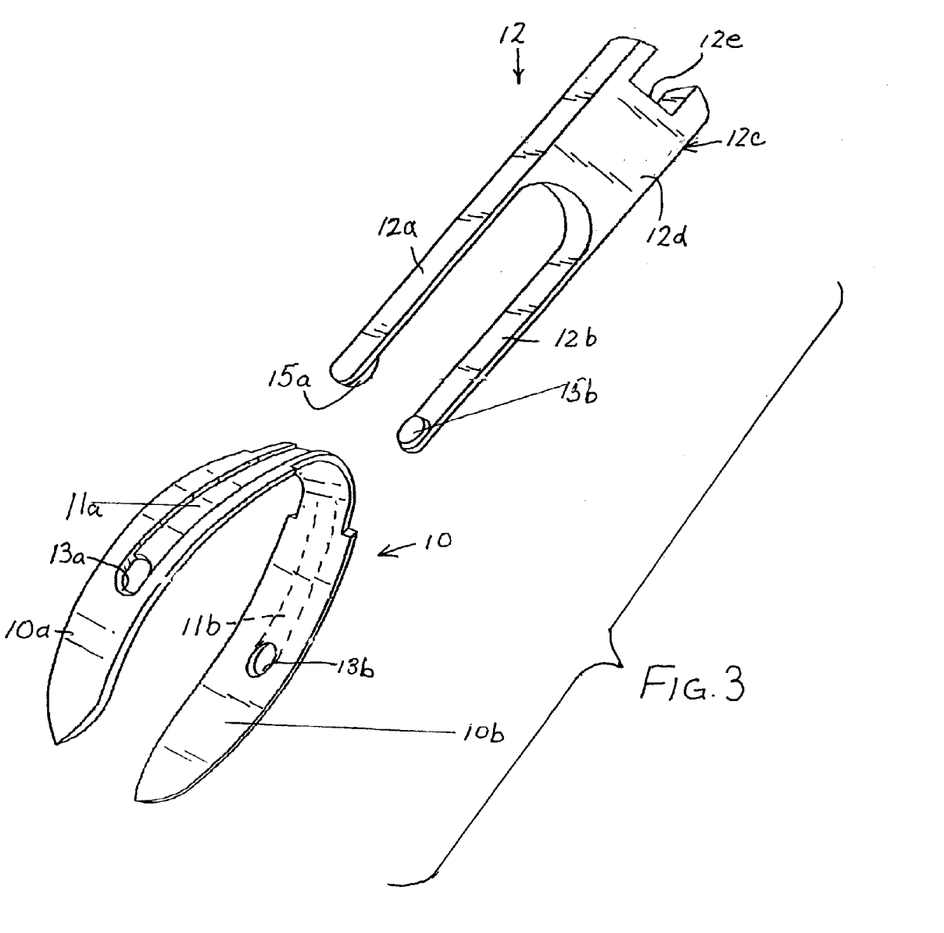
FIG. 3 is an exploded schematic perspective view showing the staple and the backbone of FIGS. 1 and 2.

FIG. 3 is a perspective view of staple 10 which is composed of a flexible metal that allows for repeat opening and closing of staple 10. Legs 10a and 10b of staple 10 are joined at the proximal end or formed by bending or folding a single metal component at a center point. Staple legs 10a and 10b have preformed channels 11a and 11b on the outside surfaces of the legs. Notches 13a and 13b communicate with the respective channels or grooves 11a and 11b. Channels 11a and 11b serve to guide legs 12a and 12b of backbone 12 over legs 10 and 10b of staple 10 during a distally directed staple-closing stroke of push bar 22, while notches 13a and 13b serve to guide and secure the backbone 12 and, more specifically, backbone protrusions 15a and 15b when backbone 12 is slid over the closed staple 10 in the target organic tissues. Backbone 12 is composed of rigid metal whose structural force is greater than the open angle force of staple 10. Channels 11a and 11b may be opposite end portions of a single channel or groove in the backside or outwardly facing surface (not separately labeled) of staple 10.

Figure 4:
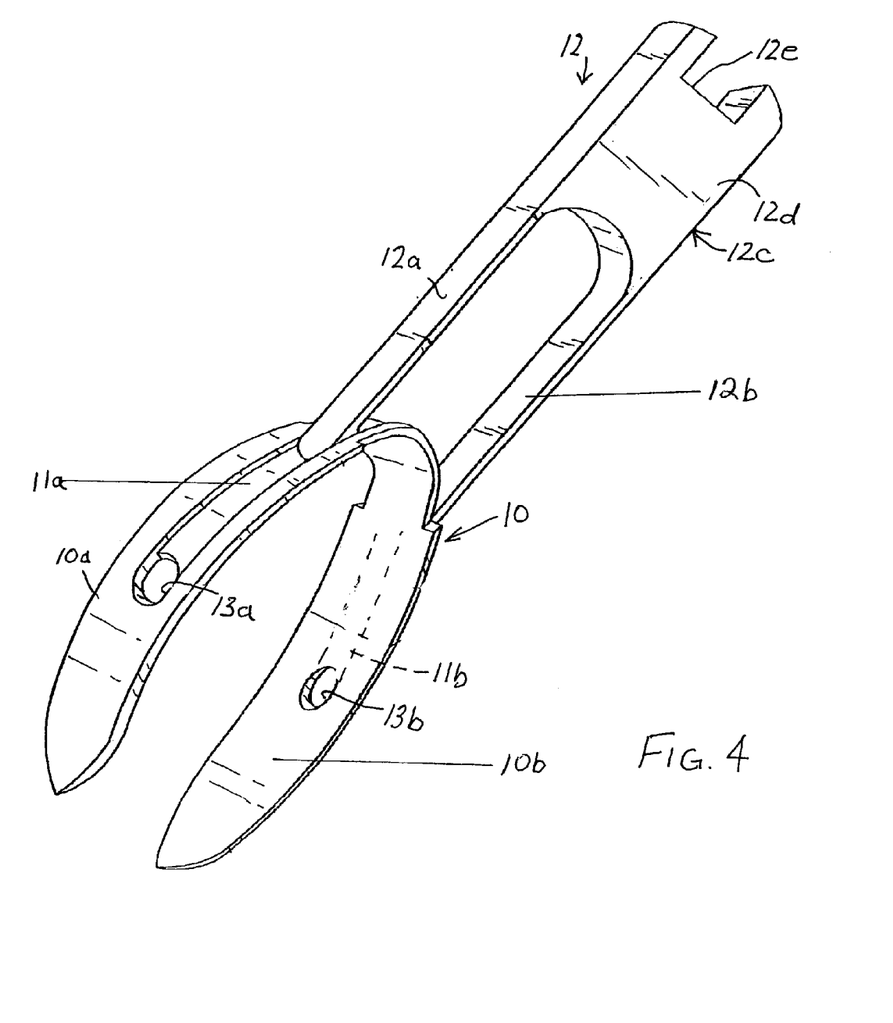
FIG. 4 is a schematic perspective view similar to FIG. 3, showing the staple in an open position with the backbone in a proximal position.

FIG. 4 is a perspective view of staple 10 and backbone 12 in proximal position to staple 10. The configuration of FIG. 4 occurs when staple holder 16 and staple 10 are partially opened after insertion of the distal end portion of assembly 8 into a patient during an endoscopic or laparoscopic surgical procedure.

Figure 5:
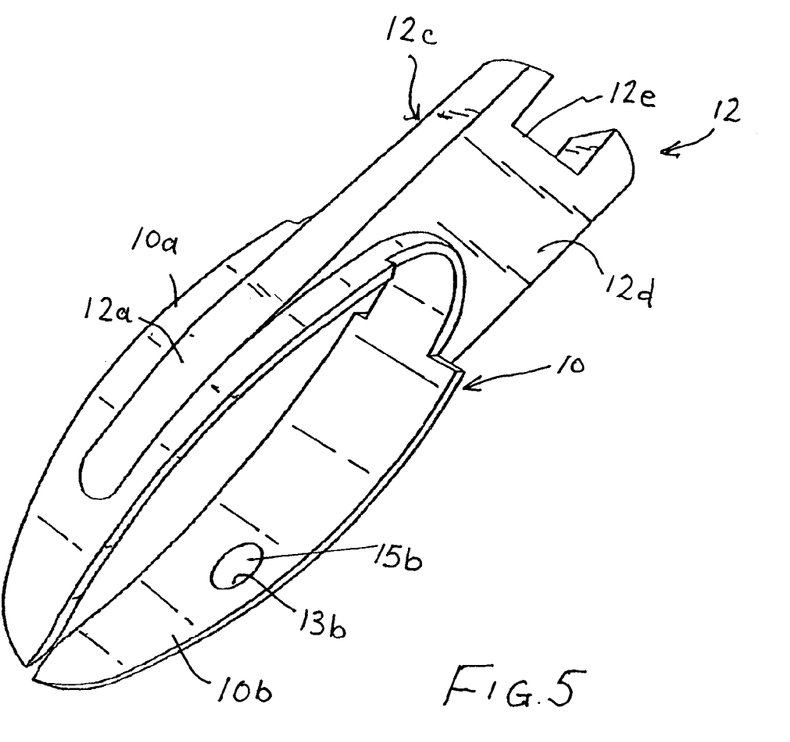
FIG. 5 is a schematic perspective view showing the staple of FIGS. 3 and 4 in a closed position with the backbone disposed over the staple, locking the staple in the closed position.

FIG. 5 is a perspective view of the backbone 12 with legs or prongs 12a and 12b disposed in the staple closed position over respective legs 10a and 10b of staple 10. Backbone 12 is slid from the proximal end of staple 10 toward the distal end of staple 10 along the preformed channels 11a and 11b in the outer walls of staple 10. Backbone protrusions 15a and 15b have diameters that match the diameters of channels 11a and 11b and of notches 13a and 13b formed in the outside surfaces or faces of staple 10. Backbone protrusions 15a and 15b lock into the respective notches 13a and 13b when backbone 12 is fully pushed down channels 11a and 11b of staple 10 in the closed position. Backbone 12 locks in place, maintaining staple 10 in a fully closed position over the captured tissue.

Figure 6:
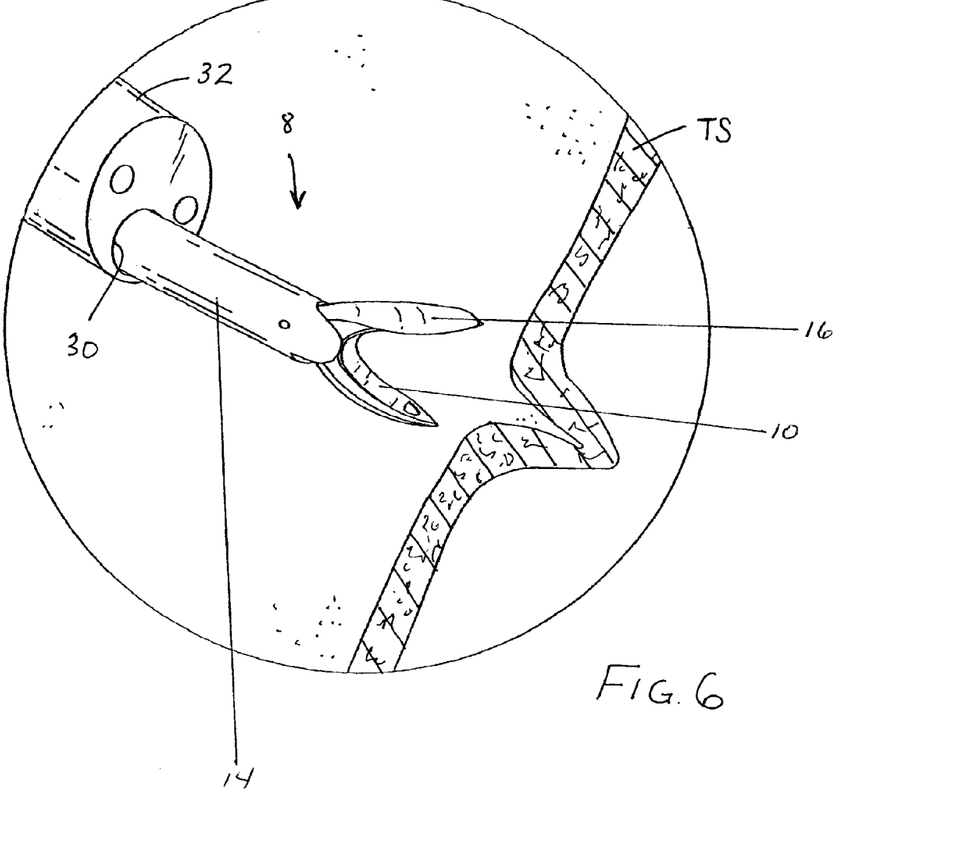
FIG. 6 is a schematic perspective view showing the staple and stapler device of FIGS. 1 and 2 approaching tissue to be secured

FIG. 6 is a perspective view of the distal end of endoscopic stapling device or assembly 8 as the device is passed through a working channel 30 of an endoscope 32 and approaches target tissue TS. Staple holder 16 is opened by manipulation of handle 24 (FIGS. 10A–10E) after the holder emerges from the distal end of the endoscope 32. In the opened configuration of holder 16 shown in FIG. 7, the staple 10 and the backbone 12 have the configurations and relative positions shown in FIG. 4.

It is to be noted that staple holder 16 has a pointed distal end for penetrating the targeted tissue. More particularly, holder jaws 16a and 16b have pointed tips 16e and 16f that enable a deep penetration of jaws 16a, 16b and concomitantly staple 10 into the target tissue TS.

Figure 7:
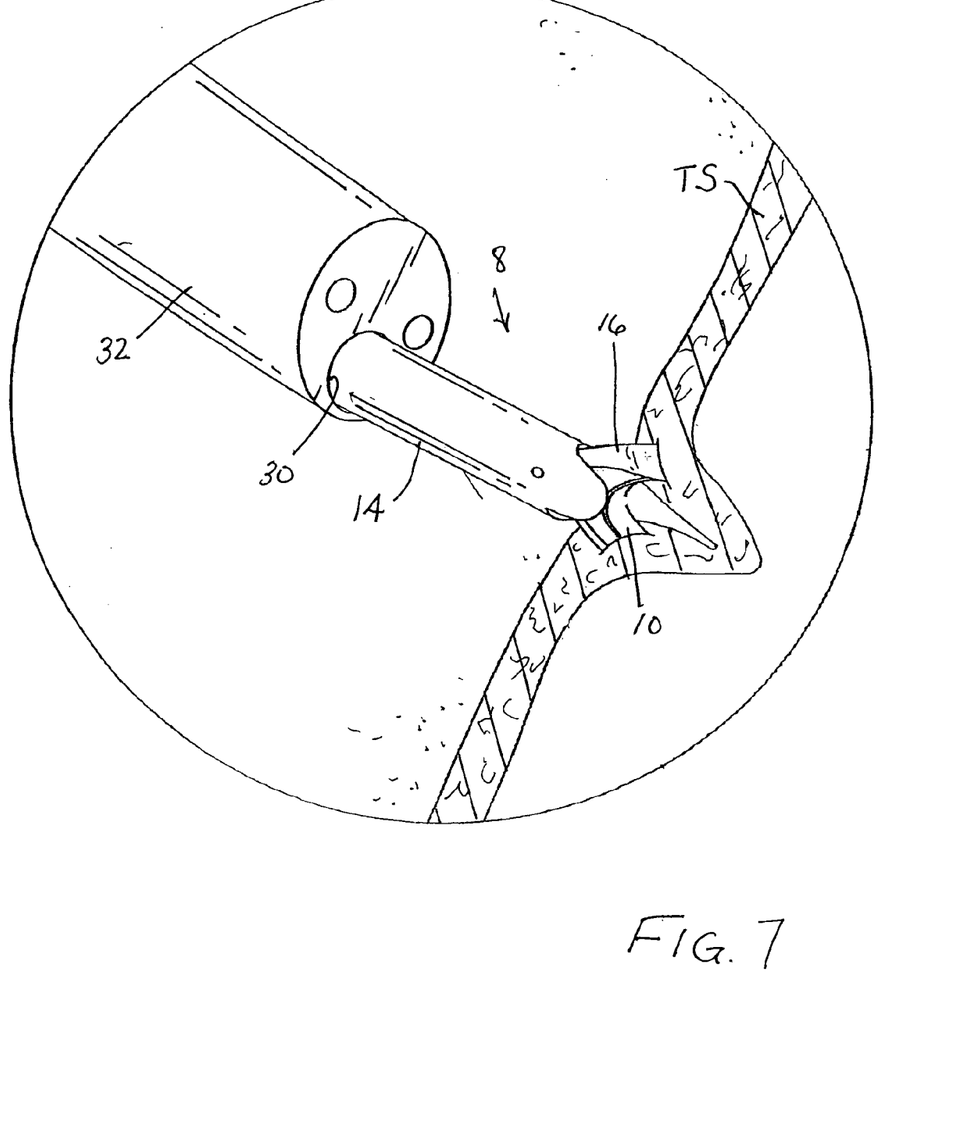
FIG. 7 is a schematic perspective view showing the staple and stapler device inserted into tissue to be secured

FIG. 7 is a perspective view of the distal end of endoscopic stapling device 8 as the jaws 16a and 16b, together with staple 10, penetrate the targeted tissue TS. When the tissue TS is located by the endoscopist, staple holder 16, in the open position, is pushed into the tissue. Staple 10 and backbone 12 still have the configurations and relative positions of FIG. 4.

Figure 8:
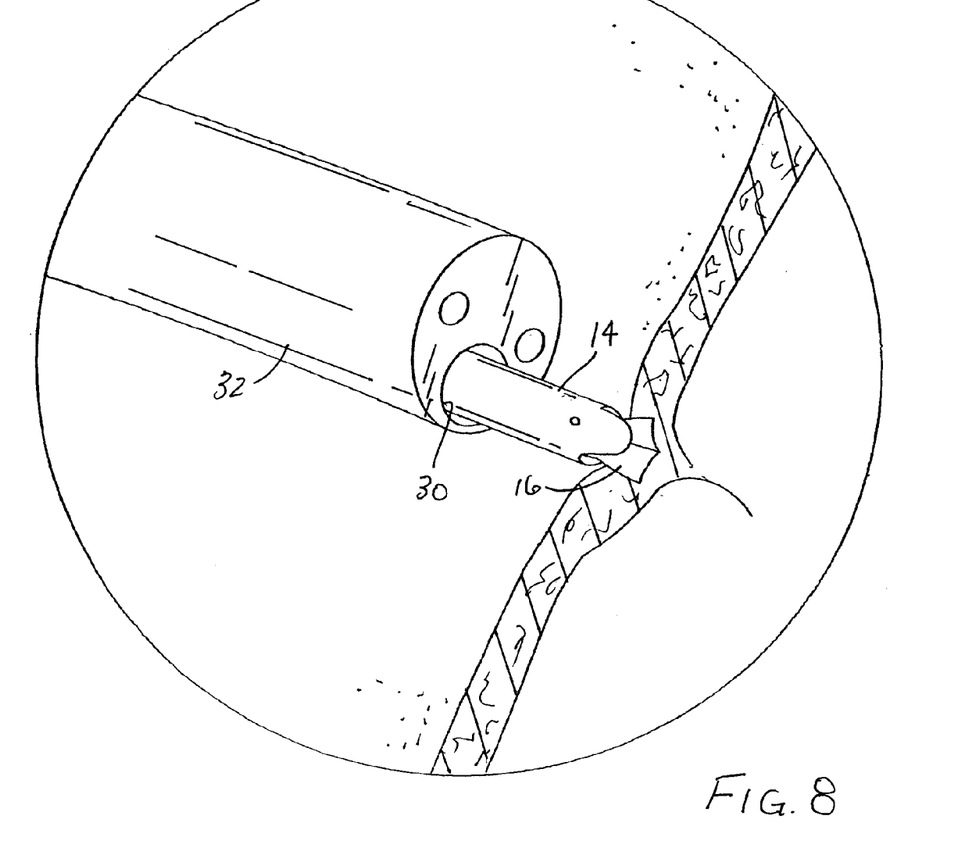
FIG. 8 is a schematic perspective view showing the staple and stapler in closed position securing tissue

FIG. 8 is a perspective view of the distal end of the endoscopic stapling device 8 as the staple holder 16 is closed over the captured tissue TS. The closure of holder 16 causes staple 10 to close as well. Staple holder 16 is closed by manipulation of the device handle 24, capturing the targeted tissue TS. More specifically, this closure may be effectuated, for instance, by drawing wires or rods 26 in a proximal direction. Handle 24 is then manipulated in a second movement, which shifts the push bar 22 in the distal direction and consequently advances the backbone 12 over the closed staple 10 that is inside the staple holder 16. Backbone 12 locks in place on the closed staple 10, as discussed above with references to FIGS. 2 and 5, and secures the captured tissue TS. Staple holder 16 is then opened by a reverse manipulation of the handle 24 and removed from the tissue. Staple 10 and backbone 12 remain on the captured tissue.

Figure 9:
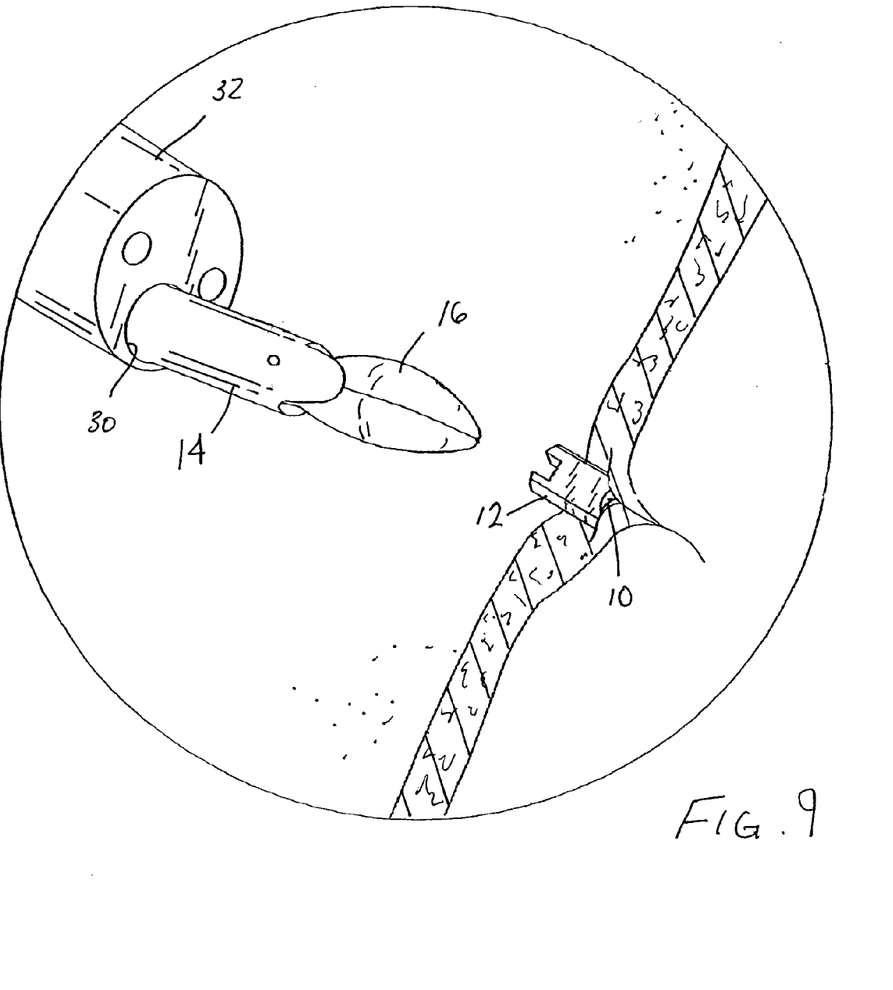
FIG. 9 is a schematic perspective view showing the staple and backbone deployed into tissue and released from stapler.

FIG. 9 is a perspective view of the distal end of the endoscopic stapling device 8 after deployment of staple 10 and backbone 12. Staple holder 16 is closed by manipulation of handle 24 and pulled back through the endoscope working channel 30.

FIGS. 10A–10E are partially schematic elevational views of the handle mechanism 24 at a proximal end of an endoscopic stapling device 34. FIGS. 10A–10E are also partially schematic cross-sectional views of a stapling mechanism 36 at a distal end of the endoscopic stapling device 34. FIGS. 10A–10E shows successive steps in the utilization of the device.

As shown in FIGS. 10A–10E, stapling device 34 includes elongate tube 38 fixed at a proximal end to handle mechanism 24. A staple holder 40 similar to staple holder 16 is connected to elongate tube 38 and an actuation assembly which includes a drive wire or rod 42 that activates jaws 40a and 40b of the staple holder 40. This actuation mechanism is connected at its proximal end to handle mechanism 24.

Handle mechanism 24 is composed of formed plastic or metal components that slide within each other. One set of components 44 controls the opening and closing of the staple holder jaws 40a and 40b another set of components 46 controls the sliding of a push bar 48 that advances a backbone 50 over a staple 52 once the staple has been inserted and closed in target tissue. Backbone 50 and staple 52 have interacting locking structures as described above particularly with references to FIGS. 3–5.

Drive wire or rod 42 effectuates the closing of jaws 40*a* and 40. Like jaws 16*a* and 16*b*, jaws 40*a* and 40*b* may be provided with a biasing spring (not shown) tending to open the jaws upon an ejection thereof into a body cavity. Alternatively, drive wire or rod 42 may be used to both open and close the jaws 40*a* and 40*b* in response to distal and proximal movement of actuation component 44 under the direct control of the operator. Jaws 40*a* and 40*b* may be connected to another tube (not shown) internal to tube 38.

Figure 10A:
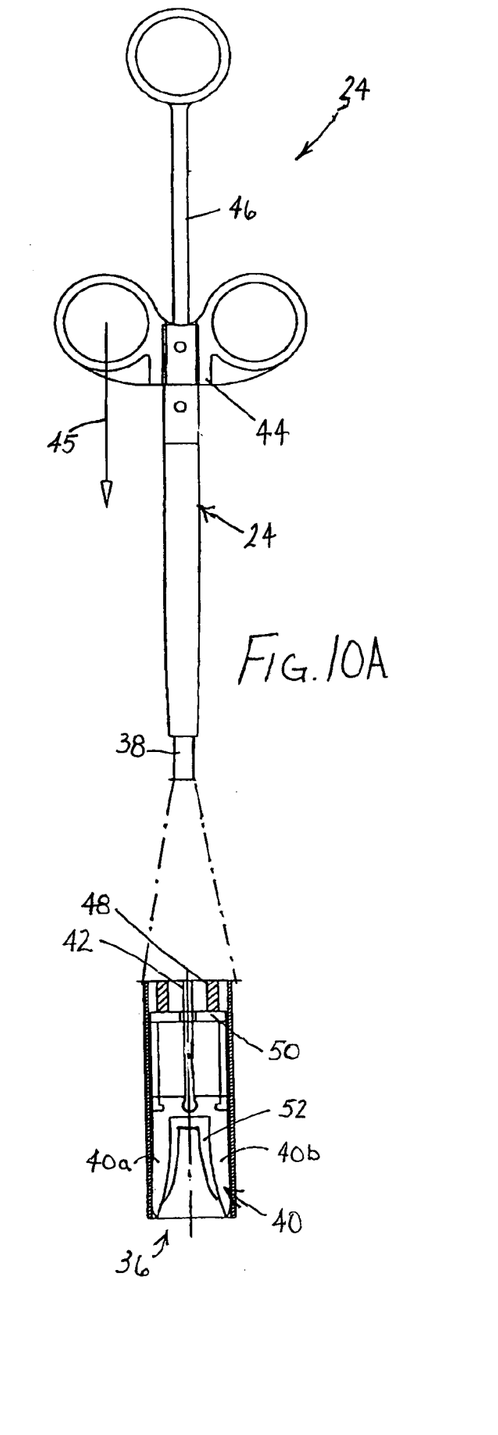
FIGS. 10A–10E are partially schematic side elevational views of a proximal end and partially schematic cross-sectional views of a distal end of an endoscopic stapling device in accordance with the present invention, showing successive steps in the utilization of the device.
Figure 10B:
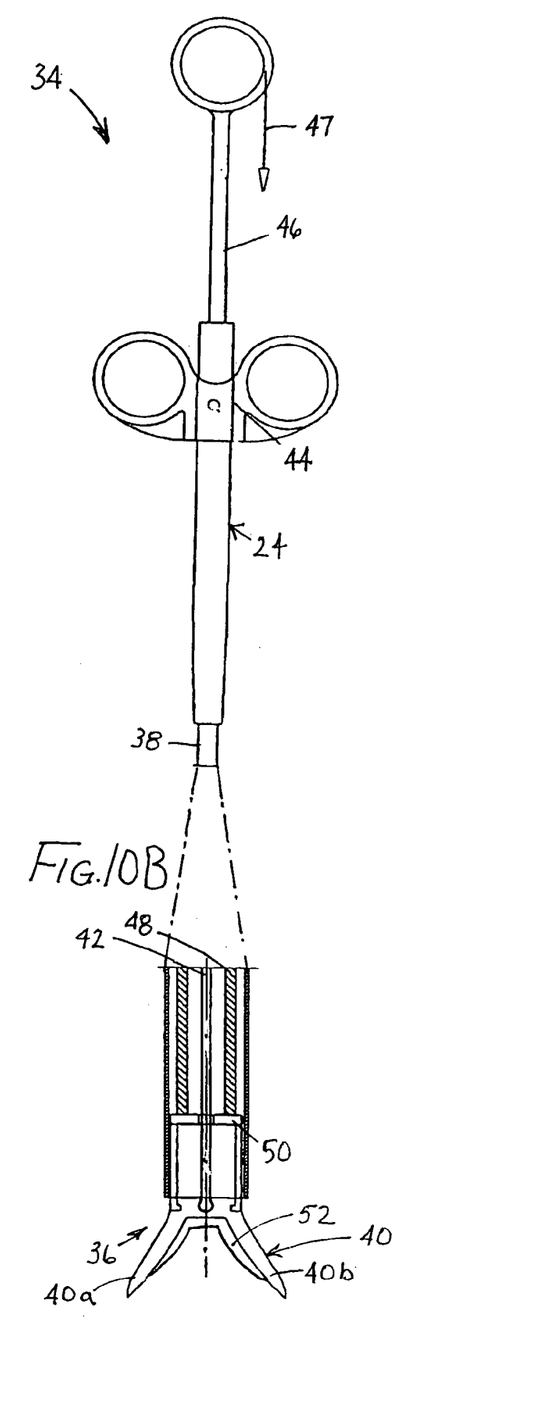
Figure 10C:
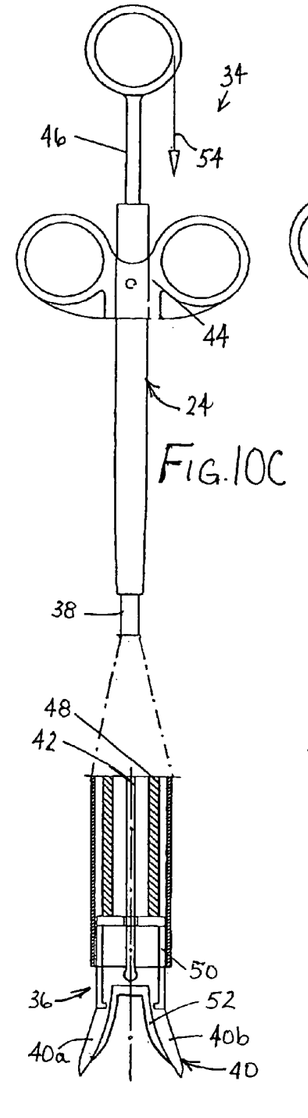
Figure 10D:
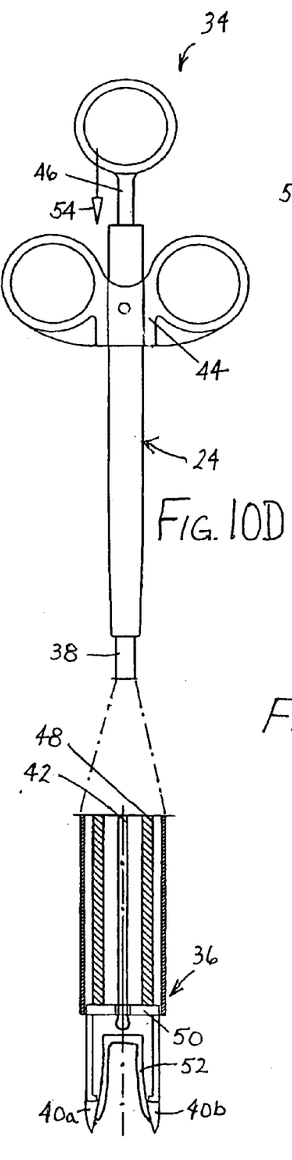
Figure 10E:
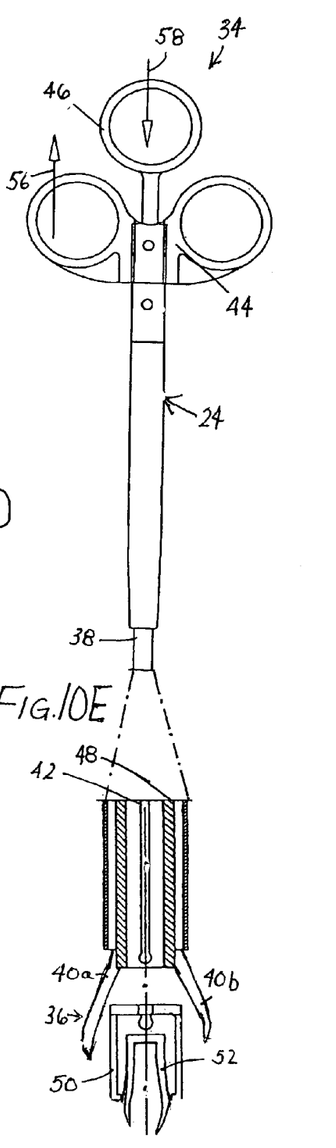

FIG. 10A shows staple 52 and staple holder 40 disposed within the distal end of tube 38 prior to ejection therefrom during an endoscopic or laparoscopic stapling procedure. FIG. 10B shows staple 52 and staple holder 40 opened by a controlled distal movement of actuation components 44 and 46 (arrows 45 and 47 in FIGS. 10A and 10B). Staple 52 is now opened with backbone 50 disposed proximally thereof, as discussed above with reference to FIG. 4. After an insertion of the opened staple holder 40 and staple 52 into a desired tissue site (see FIGS. 7 and 8, actuation component 44 is manipulated to close jaws 40*a* and 40*b* and actuation component 46 is pushed in the distal direction, as indicated by an arrow 54 to cause push bar 48 to advance backbone 50 over staple 50 (FIGS. 10C and 10D), as discussed above with reference to FIGS. 5 and 8. After the locking of staple 52 by backbone 50, actuation components 44 and 46 are moved in opposing directions, as indicated by arrows 56 and 58 in FIG. 10E, to eject backbone 50 and close jaws 40*a* and 40*b*.

Figure 11:
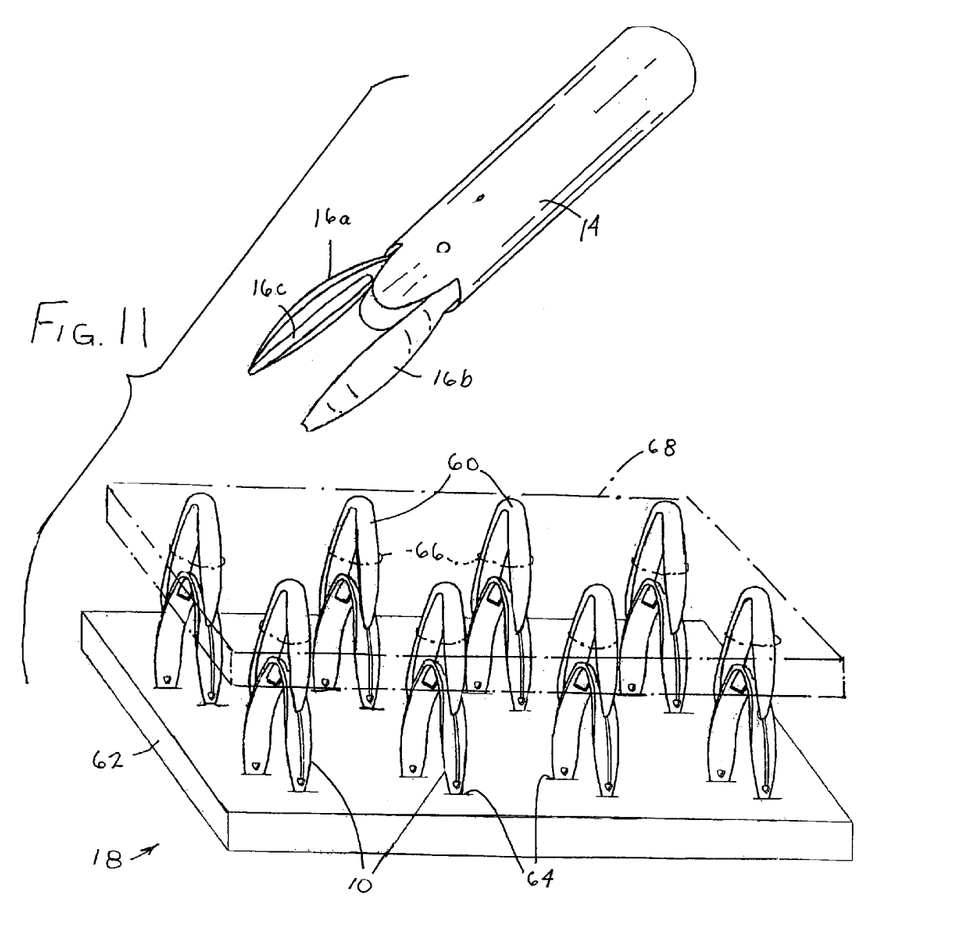
FIG. 11 is a schematic perspective view showing a staple tray assembly in accordance with the present invention.

FIG. 11 is a perspective view of a staple tray 18, which is a formed holder that contains additional staples 10 (or 52) and backbones 60 and facilitates in the reloading of staple holder 16 (or 40). Staple tray 18 has a base 62 formed with a series of holes or slots 64, which accept the distal tips of staples 10 in the open configuration thereof. A second level 68 of staple tray 18 is positioned securely over the base 62 of the staple tray 18 and has a series of aligned holes 66 that securely hold backbones 60 in proximal contact to staples 10. The second tray level 68 thus serves as an orientation structure for maintaining a plurality of backbones 60 at proximal ends of the staples 10 in the base 62 of the tray 18. When reloading staple holder 16, the staple holder is placed at the proximal end of backbone 60, push bar 22 (or 48) is retracted and staple holder 16 is slid over staple 10 capturing staple 10 in the opposing slots 16*c*, 16*d* on the inside surfaces of the staple holder jaws 16*a* and 16*b*.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. An endoscopic stapling assembly for securing tissue internal to the body, utilizing a flexible endoscope, comprising:
a staple for clamping or securing tissue inside of the body;
means operatively engageable with said staple for securing said staple in a closed position once staple is positioned and closed on desired tissue, said means for securing said staple in said closed position including a backbone made of rigid material having a pair of legs slidable over a backside of said staple and securable firmly over the closed staple, said legs having inwardly extending protrusions engageable in notches or recesses provided in said staple for locking into place over said closed staple;
a tubular member carrying active stapler components; and
means, operatively connected to said tubular member, for holding said staple during deployment thereof and manipulating said staple into an open or closed position, said active stapler components being operatively connected to said means for holding and manipulating, for operating same.

2. The endoscopic stapling assembly in accordance with claim 1, wherein said staple is biased to an open position having an open-position angle greater than an open-position angle of the staple holder component.

3. The endoscopic stapling assembly in accordance with claim 2, wherein said staple is insertable into tissue for clamping together opposing segments of tissue.

4. The endoscopic stapling assembly in accordance with claim 2, wherein said staple is made from shape memory or flexible metal.

5. The endoscopic stapling assembly in accordance with claim 2 wherein said staple is configured with opposing legs of a single folded over material, said legs being formed in an arc configuration, said legs having distal tips that touch one another when said staple is in a closed position, said distal tips of said legs being pointed.

6. The endoscopic stapling assembly in accordance with claim 1, wherein said means for securing said staple in a closed position includes means for advancing said backbone over said staple, said means for advancing including a push bar, said push bar being connected to a handle mechanism at a proximal end of said tubular member.

7. The endoscopic stapling assembly in accordance with claim 1, wherein said means for holding and manipulating comprises formed metal components connected to a drive-wire and handle mechanism.

8. The endoscopic stapling assembly in accordance with claim 7 wherein said formed metal components are comprised of opposing jaws, whereby opposing faces or surfaces of the jaws are formed to securely hold said staple, and wherein said jaws are adapted to enter and grasp tissue.

9. The endoscopic stapling assembly in accordance with claim 8 wherein distal ends of said jaws are pointed for enabling said jaws to enter targeted tissue, said means for holding and manipulating including means for operating said jaws to clamp the staple closed over the tissue, said jaws being provided along mutually facing surfaces with grooves for seating said staple.

10. The endoscopic stapling assembly in accordance with claim 8 wherein jaws are attached to a drive mechanism that opens and closes said jaws, said drive mechanism being attached to a handle mechanism.

11. The endoscopic stapling assembly in accordance with claim 8, further comprising means for holding additional staples to facilitate loading of said additional staples into said means for holding and manipulating, wherein said jaws are re-loadable with additional staples and backbone locking elements from said means for holding additional staples.

12. The endoscopic stapling assembly in accordance with claim 1, wherein said tubular member has a proximal end connected to an actuation and handle mechanism, said tubular member comprising at least one lumen-forming elongate tube made of a flexible material and having said proximal and a distal end.

13. The endoscopic stapling assembly in accordance with claim 1, wherein said means for holding and manipulating includes a pair of opposed jaws and a drive mechanism operatively coupled to said jaws, said drive mechanism comprising a handle mechanism composed of multiple sliding components and further comprising a drive-wire connected to said jaws and at least one of said sliding components, and a longitudinally displaceable push bar.

14. The endoscopic stapling assembly in accordance with claim 1, further comprising means for holding additional staples to facilitate loading of said additional staples into said means for holding and manipulating, wherein said means for holding additional staples comprises a tray with preformed holes to securely hold staples in an open configuration, said tray also provided with orientation structure for maintaining a plurality of backbones at proximal ends of the staples in said tray, said backbones being locking elements engageable with the respective staples to maintain the staples in a closed post-firing configuration.

15. An endoscopic staple and stapler assembly for securing tissue internal to the body, comprising:
   a staple holder component;
   a staple capable of being opened and closed, said staple being releasably held by said staple holder component, said staple being biased to an open position, said staple having a biased open position angle that is greater then an open position angle of the staple holder component, said staple being insertable into organic tissue for clamping together opposing segments of said tissue, said staple being made from shape memory or flexible metal, said staple having opposing legs of a single folded over member, said legs being formed in an arc configuration, said distal tips of said legs being pointed for the purpose of clamping or entering tissue for securing tissue inside of the body;
   a backbone made of rigid material, slidable over a backside of said staple, said staple having notches along said backside to guide, accept, and secure said backbone firmly over the staple in a closed position once said staple is positioned and closed on desired tissue;
   a pusher member, for advancing the backbone over said staple, said pusher member being temporarily coupled to said backbone;
   said staple holder component including a pair of formed opposing jaws, opposing edges of said jaws being formed to securely hold said staple, said jaws being attached to a drive mechanism that opens closes said jaws;
   an elongate tube with a distal end being connected to said jaw mechanism, a proximal end connected to an actuation and handle mechanism, said elongate tube having at least one lumen and being made of a flexible material, for providing a working channel for active stapler components, securely connected to said staple holder; and
   a handle mechanism, for actuation and manipulation of invention, securely connected to said elongate tube, and operatively connected to said pusher member.

16. An endoscopic stapling assembly for securing tissue internal to the body, utilizing a flexible endoscope, comprising:
   a staple for clamping or securing tissue inside of the body;
   a backbone member operatively engageable with said staple for securing said staple in a closed position once staple is positioned and closed on desired tissue, said backbone member having a pair of legs slidable over a backside of said staple and securable firmly over the closed staple;
   a tubular member having a working channel;
   a pusher member at least partially disposed in said working channel; and
   jaws operatively connected to said tubular member for holding said staple during deployment thereof and manipulating said staple into an open or closed position,
   said backbone member being provided at a proximal end with a cutout out or recess receiving said pusher member.

17. An endoscopic stapling assembly for securing tissue internal to the body, utilizing a flexible endoscope, comprising:
   a staple for clamping or securing tissue inside of the body;
   means operatively engageable with said staple for securing said staple in a closed position once staple is positioned and closed on desired tissue;
   means for carrying active stapler components; and
   means, operatively connected to said means for carrying, for holding said staple during deployment thereof and manipulating said staple into an open or closed position, said active stapler components being operatively connected to said means for holding and manipulating, for operating same,
   wherein said means for holding and manipulating comprises opposing jaws having opposing faces or surfaces formed to securely hold said staple.

18. The endoscopic stapling assembly in accordance with claim 17 wherein distal ends of said jaws are pointed for enabling said jaws to enter targeted tissue, said means for holding and manipulating including means for operating said jaws to clamp the staple closed over the tissue, said jaws being provided along mutually facing surfaces with grooves for seating said staple.

19. A staple assembly for use in rigid or flexible endoscopy for securing tissue internal to the body comprising:
   a staple for clamping or securing tissue inside of the body, said staple being provided on an outer side, along each of two oppositely facing surfaces, with a smooth groove segment and a notch at a distal end of the respective groove segment; and
   a backbone element, engageable with said staple, for locking the staple in a closed position once the staple is positioned and closed on desired tissue, said backbone element including a pair of substantially rigid legs each having a protrusion extending towards the other leg and engageable in the notch on a respective one of said oppositely facing surfaces, said backbone element being provided on a proximal side with a recess or seat for coupling to a pusher member.

20. The staple assembly in accordance with claim 19, wherein said staple is biased to an open position, said staple having a biased open position angle that is greater then an open position angle of a staple holder component.

21. The staple assembly in accordance with claim 19, wherein said staple is made from shape memory or flexible metal.

22. The staple assembly in accordance with claim 19 wherein said staple includes opposing legs of a single folded over member, said legs being formed in an arc configuration, said legs having distal tips that touch when said legs are in a closed position, said distal tips of said legs being pointed.

23. The staple assembly in accordance with claim 19, wherein said staple is insertable into tissue for clamping together opposing segments of the tissue.

* * * * *